(12) United States Patent
Meyer (10) Patent No.: US 9,006,486 B2
(45) Date of Patent: Apr. 14, 2015

(54) SYNTHESIS OF $N^1,N^3$-BIS(2,3-DIHYDROXYPROPYL)-5-NITROISOPHTHALAMIDE

(71) Applicant: Mallinckrodt LLC, Hazelwood, MO (US)

(72) Inventor: James R. Meyer, St. Louis, MO (US)

(73) Assignee: Liebel-Flarsheim Company LLC, Hazelwood, MO (US)

( * ) Notice: Subject to any disclaimer, the term of this patent is extended or adjusted under 35 U.S.C. 154(b) by 0 days.

(21) Appl. No.: 14/149,027

(22) Filed: Jan. 7, 2014

(65) Prior Publication Data

US 2014/0200367 A1     Jul. 17, 2014

Related U.S. Application Data

(60) Provisional application No. 61/752,473, filed on Jan. 15, 2013.

(51) Int. Cl.
*C07C 231/02*     (2006.01)

(52) U.S. Cl.
CPC ............................... *C07C 231/02* (2013.01)

(58) Field of Classification Search
CPC ....................................................... C07C 231/02
USPC ........................................................... 564/134
See application file for complete search history.

(56) References Cited

U.S. PATENT DOCUMENTS

| | | | |
|---|---|---|---|
| 6,153,771 A * | 11/2000 | Lane et al. | 549/552 |
| 6,441,235 B1 | 8/2002 | Parady et al. | |
| 7,244,864 B2 * | 7/2007 | Anelli et al. | 564/134 |

* cited by examiner

*Primary Examiner* — Shailendra Kumar (57) ABSTRACT

The present disclosure generally relates to a new process for the preparation of high purity 5-nitro-isophthalamide compounds, which are useful as intermediates for the preparation of imaging agents, such as iodinated x-ray contrast imaging agents like ioversol, iohexyl and iopamidol.

18 Claims, 2 Drawing Sheets

SYNTHESIS OF N¹,N³-BIS(2,3-DIHYDROXYPROPYL)-5-NITROISOPHTHALAMIDE

CROSS-REFERENCE TO RELATED APPLICATIONS

This patent application is a non-provisional patent application of, and claims priority to, U.S. Provisional Patent Application Ser. No. 61/752,473 entitled "IMPROVED SYNTHESIS OF N¹,N³-BIS(2,3-DIHYDROXYPROPYL)-5-NITROISOPHTHALAMIDE," which was filed on 15 Jan. 2013, and which is incorporated by reference in its entirety.

BACKGROUND OF THE DISCLOSURE

The present disclosure generally relates to a new process for the preparation of high purity 5-nitro-isophthalamide compounds, which are useful as intermediates for the preparation of imaging agents, such as iodinated x-ray contrast imaging agents like ioversol, iohexyl and iopamidol.

5-nitro-isophthalamide compounds (also generally referred to herein as "diamides") of general formula (2) below, where R is a $C_1$ to $C_{18}$ straight or branched chain hydrocarbyl or substituted hydrocarbyl moiety, are useful synthetic intermediates for the preparation of organoiodine compounds, such as ioversol, iohexyl and iopamidol.

(2)

Compounds of formula (2) are typically prepared by contacting a 5-nitro-isophthalate compound of formula (1) below (i.e., a "diester"), where $R^1$ and $R^2$ are independently a $C_1$ to $C_{18}$ straight or branched chain hydrocarbyl or substituted hydrocarbyl moiety, with a stoichiometric excess of at least 10% of a primary amine of formula $RNH_2$ in a suitable solvent. (See, e.g., U.S. Pat. No. 7,244,864, the entire contents of which are incorporated herein by reference for all relevant and consistent purposes.)

(1)

Typically, a ratio of primary amine to diester of greater than 2.2:1, on a molar equivalent basis, is required to achieve a commercially acceptable yield of diamide formula (2). Problematically, diamide reaction mixtures prepared by such a process typically contain relatively high amounts of unreacted diester and primary amine, as well as substantial quantities of reaction impurities, that must be removed in subsequent purification steps to generate a diamide of suitable purity. Impurities include the acid amide of formula (3), and amide esters of formulae (4) and (5) below:

(3)

(4)

and

(5)

In contrast to the process as outlined above, U.S. Pat. No. 6,441,235 B1 (to Parady, et al.) discloses an alternative process for the preparation of diamides of formula (2). In the this process, one molar equivalent of diester of formula (1) is reacted with 2.1 molar equivalents of a primary amine in a solvent system comprising a basic catalyst, at a temperature of between 65° C. and 150° C. and at the boiling point (i.e., reflux temperature) of the solvent system. Problematically, the Parady et al. process is run at relatively dilute concentrations, utilizes a significant stoichiometric excess of primary amine, and high reaction temperature, and thus generates a reaction product mixture having high levels of the acid amide and amide ester impurities.

Accordingly, a need continues to exist for an improved method for preparing 5-nitro-isophthalamide compounds in high yield, purity and throughput.

SUMMARY OF THE DISCLOSURE

Briefly, therefore, the present disclosure is directed to a process for preparing a diamide compound of formula (2). The process comprises: (i) forming a reaction mixture comprising a diester of formula (1), (1)

a primary amine of formula $RNH_2$, a basic catalyst and a solvent; and, (ii) heating the reaction mixture to a reaction temperature of from about 25° C. to less than 65° C. and holding the reaction mixture at the reaction temperature for a reaction time sufficient to generate a reaction product mixture comprising diamide compound formula (2)

(2)

wherein R, $R^1$ and $R^2$ are independently selected from $C_1$ to $C_{18}$ straight or branched chain hydrocarbyl or substituted hydrocarbyl moieties, and, the molar ratio of the primary amine to the diester is from 2:1 to about 2.4:1.

The present disclosure is further directed to a high purity diamide compound of formula (2)

(2)

produced by a process comprising: (i) carrying out the process as detailed above; and, (ii) isolating the diamide compound, wherein the high purity diamide compound contains less than about 0.1% by weight of diester of formula (1)

(1)

less than about 2% by weight of acid amide of formula (3)

(3)

and less than about 0.1% by weight of combined amide esters of formula (4) and (5)

(4)

and (5)

wherein R, $R^1$ and $R^2$ are independently selected from $C_1$ to $C_{18}$ hydrocarbyl or substituted hydrocarbyl moieties.

DETAILED DESCRIPTION OF THE DISCLOSURE

The present disclosure is directed to an improved method for preparing 5-nitro-isophthalamide compounds ("diamides") from 5-nitro-isophthalate compounds and a primary amine in the presence of a basic catalyst. More particularly, in accordance with the present disclosure, high purity 5-nitro-isophthalamide can be prepared by utilizing: (i) a ratio of molar equivalents of the primary amine to the 5-nitro-isophthalate compound of between 2:1 and about 2.4:1; and (ii) a reaction temperature of from about 25° C. to less than 65° C. The reaction scheme for the preparation of diamide compounds (of formula (2)) from diester compounds (of formula (1)), in accordance with the present disclosure, is generally depicted below:

REACTION SCHEME (1)

wherein R, $R^1$ and $R^2$ are independently selected from $C_1$ to $C_{18}$ straight or branched chain hydrocarbyl or substituted hydrocarbyl. Each of these compounds and the related synthetic steps are described in more detail below.

In this regard, it is to be noted that, as further detailed below, in addition to the diamide product of formula (2), impurities such as those including at least one of the diester of formula (1), the acid amide of formula (3), and the amide esters of formulae (4) and (5), all as illustrated below, may also be present in the product reaction mixture (resulting from the process as outlined herein) as product contaminants of the diamide of formula (2):

A. 5-Nitro-Isophthalate Compounds 5-nitro-isophthalate (diester) compounds of formula (1) within the scope of the present disclosure include compounds wherein $R^1$ and $R^2$ are independently selected from a $C_1$ to $C_{18}$ straight or branched chained hydrocarbyl or substituted hydrocarbyl moieties. In some other embodiments, $R^1$ and $R^2$ are independently selected from $C_1$-$C_{12}$, or $C_1$-$C_{10}$, or $C_1$-$C_8$, or $C_1$-$C_6$, straight or branched chain hydrocarbyl or substituted hydrocarbyl moieties. In some particular embodiments, $R^1$ and $R^2$ are independently selected the group consisting of methyl, ethyl, n-propyl, i-propyl, n-butyl, i-butyl and t-butyl. In more particular embodiments, $R^1$ and $R^2$ are methyl (—$CH_3$).

B. 5-Nitro-Isophthalamide Compounds And Primary Amine 5-nitro-isophthalamide compounds of formula (2) and primary amine compounds within the scope of the present disclosure include compounds wherein R is a $C_1$ to $C_{18}$ straight or branched hydrocarbyl or substituted hydrocarbyl moieties. In some particular embodiments, R is $C_1$-$C_{12}$, or $C_1$-$C_{10}$, or $C_2$-$C_8$, or $C_2$-$C_6$, straight or branched hydrocarbyl or substituted hydrocarbyl moieties. In some particular embodiments, the hydrocarbyl is substituted with at least one hydroxyl moiety. In more particular embodiments, R is selected from the group consisting of 2-hydroxyethyl, 2,3-dihydroxypropyl, 3-hydroxypropyl, 3,4-dihydroxybutyl, 4-hydroxybutyl or 1,3-dihydroxyisopropyl, wherein propyl may be n-propyl or i-propyl and butyl may be n-butyl, i-butyl or t-butyl. In other particular embodiments, R is 2,3-dihydroxy-n-propyl (—$CH_2CH(OH)CH_2OH$) or 2,3-dihydroxy-1-propyl (—$CH(CH_2OH)_2$).

C. Solvent

Suitable solvents may be selected from various alcohols and amides generally known to those of ordinary skill in the art. In some particular embodiments, the solvent comprises, or is selected from, methanol, ethanol, 1-propanol, 2-propanol, 1-butanol, 2-butanol, 2-methoxymethanol, 2-ethoxyethanol, 3-methoxypropanol, formamide, N-methylformamide, and combinations or mixtures thereof. In other particular embodiments, the solvent comprises, or is selected from, methanol, ethanol, 1-propanol and 2-propanol. In yet other particular embodiments, the solvent is methanol.

D. Base Catalyst

Suitable base catalysts may be selected from a salt of an alkali metal and an alkoxide, or a salt of an alkaline earth metal and an alkoxide, generally known to those of ordinary skill in the art, or some combination or mixture thereof. The base may optionally be derived by the addition of an alkali metal to a lower-aliphatic alcohol. In some particular embodiments, the metal is selected from sodium, potassium, lithium and magnesium. In more particular embodiments, the alkoxide is selected from methoxide, ethoxide, i-propoxide, t-butoxide and =oxide, such as a sodium salt thereof. In various preferred embodiments, the base catalyst is sodium methoxide or sodium ethoxide in a suitable solvent (such as for example methanol).

E. Reaction Conditions

In accordance with the present disclosure, it has been discovered that 5-nitro-isophthalamide compounds of high purity can be prepared from a reaction mixture as detailed herein, at a reduced molar equivalent ratio of primary amine to diester and at a reduced reaction temperature. Surprisingly, the reaction proceeds to near completion or substantial completion under these conditions at reaction times consistent with or less than known processes run under more extreme conditions, such as at a substantial molar equivalent excess of primary amine to diester and/or elevated reaction temperatures.

In particular, the concentration of the diester of formula (1) in the reaction mixture is preferably about 1, about 2, about 3, about 4, about 5, about 6, about 7, about 8, about 9 or about 10 moles per liter, or within some range defined by two of these concentrations as end points. For example, in some embodiments, the formula (1) concentration may be from about 1 to about 10 moles per liter, from about 2 to about 10 moles per liter, from about 3 to about 10 moles per liter, from about 4 to about 10 moles per liter, or from about 4 to about 8 moles per liter.

In these or other particular embodiments, the ratio of the primary amine to the diester of formula (1) is suitably from 2:1 to about 2.40:1, on a molar equivalent basis. In various embodiments, for example, this ratio may be 2:1, about 2.1:1, about 2.2:1, about 2.3:1 or about 2.4:1, or alternatively may fall within a range bound by any two of these ratios. In some particular embodiments, the molar ratio may be within a range of from about 2.1:1 to about 2.2:1, from about 2.1:1 to about 2.3:1, or between about 2:1 and about 2.1:1 (e.g., about 2.01:1, about 2.02:1, about 2.03:1, about 2.04:1, about 2.05:1, about 2.06:1, about 2.07:1, about 2.08:1, about 2.09:1, or some range bound by two of these ratios, such as for example from about 2.01:1 to about 2.09:1, from about 2.01:1 to about 2.08:1, from about 2.03:1 to about 2.09:1, from about 2.03:1 to about 2.08:1, or from about 2.05:1 to about 2.08:1).

In these or other particular embodiments, the ratio of the basic catalyst to the diester of formula (1) is suitably from about 0.03:1 to about 0.1:1, on a molar equivalent basis. In various embodiments, for example, this ratio may be about 0.03:1, about 0.04:1, about 0.05:1, about 0.06:1, about 0.07:1, about 0.08:1, about 0.09:1 or about 0.1:1, or alternatively may fall within a range bound by any two of these ratios. In some particular embodiments, the molar ratio may be within a range of from about 0.04:1 to about 0.1:1, from about 0.05:1 to about 0.09:1, from about 0.05:1 to about 0.08:1, from about 0.06:1 to about 0.09:1, or from about 0.06:1 to about 0.08:1.

The reaction temperature is typically from about 25° C. to less than 65° C. In various embodiments, for example, this reaction temperature may be about 25° C., about 30° C., about 35° C., about 40° C., about 45° C., about 50° C., about 55° C., or about 60° C., or alternatively may fall within a range bound by any two of these temperatures. In some particular embodiments, the temperature may be within a range of from about 25° C. to about 60° C., from about 25° C. to about 55° C., from about 25° C. to about 50° C., from about 25° C. to about 40° C., or from about 25° C. to about 30° C., while in other embodiments the temperature may be within a range of from about 30° C. to about 60° C., about 30° C. to about 50° C., or about 30° C. to about 40° C.

The reaction of the present process advantageously proceeds to near completion or substantial completion, as evidenced by an essential absence of diester compound of formula (1) in the resulting reaction product mixture (as determined by means generally known in the art, such as by high pressure liquid chromatography ("HPLC") analysis) in about 1 hour, about 2 hours, about 3 hours, about 4 hours, about 6 hours, about 8 hours, about 10 hours or about 12 hours, or alternatively some duration falling within a range bound by any two of these time periods. In some particular embodiments, the reaction proceeds for a duration of about 1 hour to about 12 hours, from about 1 hour to about 8 hours, from about 1 hour to about 6 hours, from about 1 hour to about 4 hours, from about 1 hour to about 3 hours, from about 1 hour to about 2 hours, or alternatively from about 2 hours to about 6 hours, or from about 2 hours to about 4 hours. In other particular embodiments, the reaction proceeds for a duration of, for instance, about 1 hour, about 1.5 hours, about 2 hours, about 2.5 hours, about 3 hours, about 3.5 hours or about 4 hours.

F. Product Purity

As described above, 5-nitro-isophthalamide compounds of formula (2), prepared according to the process of the present disclosure, may contain as an impurity one or more of the following: unreacted 5-nitro-isophthalate compound of formula (1); unreacted primary amine; acid amides of formula (3); amide esters of formula (4); and/or, amide esters of formula (5). Product purity can be measured by any suitable analytical method known to those skilled in the art. In one method, analysis by HPLC is done on a 2-3 drop sample size diluted to 100 ml with MilliQ water with a Waters instrument and Empower software at a wavelength of 254 nm using a 4.6 mm×250 mm 10μ C18 column at 25° C. at a 3.0 ml/min flow rate of the gradient depicted in Table A below wherein Mobile Phase A is filtered MilliQ water and Mobile Phase B is 30% methanol in filtered MilliQ water. Optionally, a Shimadzu instrument and Totalchrome software may be used.

TABLE A

| Time (min) | Mobile Phase A (%) | Mobile Phase B (%) | Curve |
|---|---|---|---|
| 0 | 80 | 20 | 9 |
| 15.01 | 0 | 100 | 9 |
| 30.01 | 80 | 20 | 9 |
| 36.00 | 80 | 20 | 9 |

In various embodiments, 5-nitro-isophthalamide compounds of formula (2) comprise about 95%, about 96%, about 97%, about 98%, about 99%, or more (as determined by HPLC analysis), of the sum of compound formulae (1) through (5). In other embodiments, the content of diester formula (1) is about 1%, about 0.5%, about 0.3%, about 0.1%, about 0.05%, about 0.03%, about 0.01%, or less, by weight of the sum of the content of formulae (1) through (5), or is non-detectable. In yet other embodiments, the content of acid amide formula (3) is about 5%, about 4%, about 3%, about 2%, about 1%, or less, by weight of the sum of the content of formulae (1) through (5). In yet other embodiments, the content of amide ester of formulae (4) and (5) is about 0.5%, about 0.3%, about 0.1%, about 0.08% about 0.06%, about 0.04%, about 0.02%, about 0.01%, or less, by weight of the sum of the content of formulae (1) through (5), or is non-detectable. In one particular embodiment, the content of diamide formula (2) is about 96% by weight, or more, the content of diester formula (1) is no more than about 0.1% by weight, the content of acid amide formula (3) is no more than about 2% by weight, and the content of amide ester of formulae (4) and (5) is no more than about 0.1% by weight each, of the sum of the content of formulae (1) through (5).

G. Product Isolation

The high purity 5-nitro-isophthalamide reaction product can be isolated from the reaction product mixture by means generally known in the art. In some embodiments, solvent is removed from the reaction product mixture by distillation, leaving an oil and/or a solid. The oil and/or solid containing high purity 5-nitro-isophthalamide is then dissolved in a second solvent, such as deionized water. Although not narrowly critical to achieve the product purity characteristics of the present invention, the high purity 5-nitro-isophthalamide prepared by the process of the present invention can be optionally further purified. For instance, in some embodiments, a solution of 5-nitro-isophthalamide may be contacted with a suitable resin in an ion exchange chromatography unit operation. In some embodiments, the unreacted primary amine is retained on the resin and 5-nitro-isophthalamide elutes from the resin in the aqueous carrier phase. The resin can then be washed with additional water to rinse out retained 5-nitro-isophthalamide product followed by a suitable solvent to elute the retained unreacted primary amine. In some embodiments, the resin is an acidic cation exchange resin. In other embodiments, the acid cation exchange resin is a strong acid cation exchanger. Suitable resins include AMBERLITE® IR-120 PLUS or equivalent.

The process of the present disclosure provides a significant advance in the art. For instance, high purity 5-nitro-isophthalamide compounds can be prepared according to the process of the present disclosure, thereby obviating the need for subsequent impurity removal. Further, high purity and yield are achieved at reduced ratios of primary amine to diester, such that the various advantages of the disclosure can be achieved using only about a 3% stoichiometric excess of primary amine, as compared to 5% or more as taught by the prior art. Such a ratio results in reduced primary amine usage, thereby optimizing crude material cost and providing a diamide product having low unreacted primary amine content. Still further, the present process generates diamide having a low color body content, thereby obviating the need for removal thereof prior to downstream processing. Yet further, the present process enables reactant concentrations to be increased on the order of about five-fold, while maintaining reaction time (i.e., cycle time) and improving yield and purity, thereby providing for higher throughput using existing process equipment. Yet further, reduced reaction temperature improves energy efficiency, cycle time and product cost by minimizing heating and cooling cycles.

H. Definitions

The terms "hydrocarbon" and "hydrocarbyl" as used herein describe moieties or radicals consisting exclusively of the elements carbon and hydrogen. These moieties include, for example, alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 18 carbon atoms, or alternatively 1 to 10 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. Exemplary substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

In view of the present disclosure, it will be apparent that modifications and variations are possible in the process detailed herein without departing from the intended scope of the disclosure and as defined in the appended claims.

EXAMPLES

The following non-limiting examples are provided for illustrative purposes only, and therefore should not be viewed in a limiting sense.

Example 1

Preparation of $N^1,N^3$-bis(2,3-dihydroxypropyl)-5-nitroisophthalamide ("Diamide") at 30-35° C. Reaction Temperature In a first experiment, Dimethyl-5-nitroisophthalate (Diester) was combined with 3-aminopropanel-2-diol (APD) and 25% sodium methoxide (NaOMe) and methanol in a stirred 250 mL jacketed flask attached to a heat/cool module with a condenser. The diester concentration in the solvent was 6 moles per liter. The reactant amounts are summarized in Table 1a below, wherein the equivalent ratio of APD to Diester was 2.06:1 and the mole ratio of NaOMe catalyst to Diester was 0.1:1.

The reaction mixture was heated with agitation to a temperature between 30 to 35° C., and held within that temperature range under a nitrogen blanket for a duration of about 2 hours, whereupon the reaction was determined to be complete by HPLC analysis. The contents of the flask were then heated to 50° C. under vacuum to remove methanol by distillation. De-ionized water was added to the flask after reaction completion to dissolve the product, whereupon the product mixture was cooled to room temperature.

TABLE 1a

| Reagent | MW | Weight (g) | Volume (mL) | Moles | Equiv. |
|---|---|---|---|---|---|
| Diester | 239.18 | 50.00 | N/A | 0.209 | 1.00 |
| APD | 91.11 | 39.37 | N/A | 0.4306 | 2.060 |
| Methanol | 32.04 | N/A | 35.55 | 0.8641 | 4.113 |
| 25% NaOMe in Methanol | 54.02 | 4.54 | 4.80 | 0.021 | 0.10 |
| De-ionized Water | 18.0 | N/A | 55.00 | N/A | N/A |

HPLC analysis (under the conditions described above) indicated that the reaction mixture contained, as an approximate percentage of the total reaction products, 97.74% diamide, 0% diester, 0% amide ester and 1.7% acid amide.

The reaction was scaled up to 250 mL and 1 L, and run under the same conditions. Table 1b below provides details relating to the purity (or impurity content), as determined by HPLC, where "Diamide" refers to $N^1,N^3$-bis(2,3-dihydroxypropyl)-5-nitroisophthalamide and "Acid Amide Impurity" refers 3-(2,3-dihydroxypropylcarbamoyl)-5-nitrobenzoic acid ("Acid Amide").

TABLE 1b

| | Diamide | Acid Amide Impurity | Comment |
|---|---|---|---|
| 1 | 97.79 | 1.55 | 250 mL reaction |
| 2 | 97.64 | 1.66 | 250 mL reaction |
| 3 | 97.59 | 1.89 | 250 mL reaction |
| 4 | 97.61 | 1.80 | 1000 mL reaction |
| 5 | 97.55 | 1.87 | 1000 mL reaction |
| 6 | 97.52 | 1.80 | 1000 mL reaction |
| Maximum | 97.79 | 1.89 | — |
| Minimum | 97.52 | 1.55 | — |
| Average | 97.62 | 1.76 | — |
| Standard Deviation | 0.095 | 9.1314 | — |

Notably, these results indicate that the diester reactant and the impurity methyl-3-(2,3-dihydroxypropylcarbamoyl)-5-nitrobenate ("Amide Ester") were not detectable in the reaction product mixture. The results also indicate that a reaction temperature of 30 to 35° C., at a mole ratio of APD to diester of 2.06:1 and a diester concentration of 6 moles per liter, results in high diamide purity and low acid amide impurity levels.

Example 2

Preparation of Diamide at 60° C. Reaction Temperature

In a second experiment, diamide was prepared at a reaction temperature of 60° C. and at a ratio of APD to diamide of 2.03:1; otherwise, this reaction was carried out according to the reaction conditions for Example 1. The reactants are summarized in Table 2a, below. The reaction was repeated four times, and the results obtained are summarized in Table 2b, below (where "Exp." refers to experiment number, "Temp." is the reaction temperature in ° C., "Ratio" is the equivalent ratio of APD to Diamide, "NaOMe" is the number of equivalents of NaOMe, and the Diamide, Acid Amide, Amide Ester and Diester are reported in % purity by HPLC).

TABLE 2a

| Reagent | MW | Weight (g) | Volume (mL) | Moles | Equiv. |
|---|---|---|---|---|---|
| Diester | 239.18 | 50.00 | N/A | 0.209 | 1.00 |
| APD | 91.11 | 38.85 | N/A | 0.4249 | 2.030 |
| Methanol | 32.04 | N/A | 35.00 | 0.8641 | 4.113 |
| 25% NaOMe in Methanol | 54.02 | 0.90 | 1.00 | 0.0044 | 0.02 |
| De-ionized Water | 18.0 | N/A | 55.00 | N/A | N/A |

TABLE 2b

| Exp. | Temp. | Ratio | NaOMe | Di-amide | Acid Amide | Amide Ester | Diester |
|---|---|---|---|---|---|---|---|
| 1 | 60° C. | 2.03:1 | 0.020 | 97.18 | 2.64 | 0.03 | 0.00 |
| 2 | 60° C. | 2.03:1 | 0.020 | 94.82 | 4.78 | 0.00 | 0.00 |
| 3 | 60° C. | 2.03:1 | 0.020 | 95.01 | 4.17 | 0.00 | 0.00 |
| 4 | 60° C. | 2.03:1 | 0.020 | 94.43 | 2.21 | 0.00 | 0.00 |

Notably, these results indicate that the diester reactant and the amide ester impurity were not detectable in the reaction product mixture. The results show that a reaction temperature of 30 to 35° C. at a mole ratio of APD to diester of 2.03:1 and at a diester concentration of 6 moles per liter results in high diamide purity and low acid amide impurity levels.

Example 3

Preparation of Diamide at Various Reaction Temperatures and Ratios of APD to Diamide Diamide was prepared at various reaction temperatures ranging from 25° C. to 108° C., and at ratios of APD to diamide of 2.10:1 and 2.08:1, according to the reaction conditions reported in Table 3a, below. Experiments 1-4 were run at a diester concentration of 1.00 mole per liter in the solvent 2-methoxyethanol. Experiments 5-8 we run at a diester concentration of 3.22 moles per liter in the solvent methanol. The analytical results obtained are reported in Table 3b, below. ("Exp." refers to experiment number, "Temp." is the reaction temperature in ° C., "Time" is the reaction time in hours, "Ratio" is the molar equivalent ratio of APD to diester, "NaOMe:Diest." is molar equivalent ratio of sodium methoxide to diester. Acid Amide, Amide Ester and Diester are reported in % purity by HPLC.

TABLE 3a

| Exp. | Temp. | Time | Moles Diester | Moles APD | Ratio | NaOMe:Diest. |
|---|---|---|---|---|---|---|
| 1 | 108 | 3 | 0.209 | 0.4386 | 2.10:1 | 0.0933 |
| 2 | 108 | 3 | 0.209 | 0.4386 | 2.10:1 | 0.0933 |
| 3 | 65 | 3 | 0.209 | 0.4386 | 2.10:1 | 0.0933 |
| 4 | 30 | 3 | 0.209 | 0.4386 | 2.10:1 | 0.0933 |
| 5 | 25-30 | 2 | 0.209 | 0.4390 | 2.10:1 | 0.0746 |
| 6 | 25-30 | 2 | 0.209 | 0.4390 | 2.10:1 | 0.0885 |
| 7 | 45-50 | 3 | 0.209 | 0.4349 | 2.08:1 | 0.0603 |
| 8 | 45-50 | 3 | 0.209 | 0.4349 | 2.08:1 | 0.0603 |

TABLE 3b

| Exp. | Diamide | Acid Amide | Amide Ester | Diester |
|---|---|---|---|---|
| 1 | 86.75 | 7.55 | 0.31 | 0.00 |
| 2 | 86.78 | 8.15 | 0.30 | 0.00 |
| 3 | 95.77 | 2.65 | 0.18 | 0.00 |
| 4 | 97.68 | 1.82 | 0.00 | 0.00 |
| 5 | 98.20 | 1.23 | 0.00 | 0.00 |
| 6 | 97.77 | 1.56 | 0.07 | 0.00 |
| 7 | 97.65 | 1.75 | 0.03 | 0.00 |
| 8 | 97.80 | 1.63 | 0.00 | 0.00 |

Figure 1:
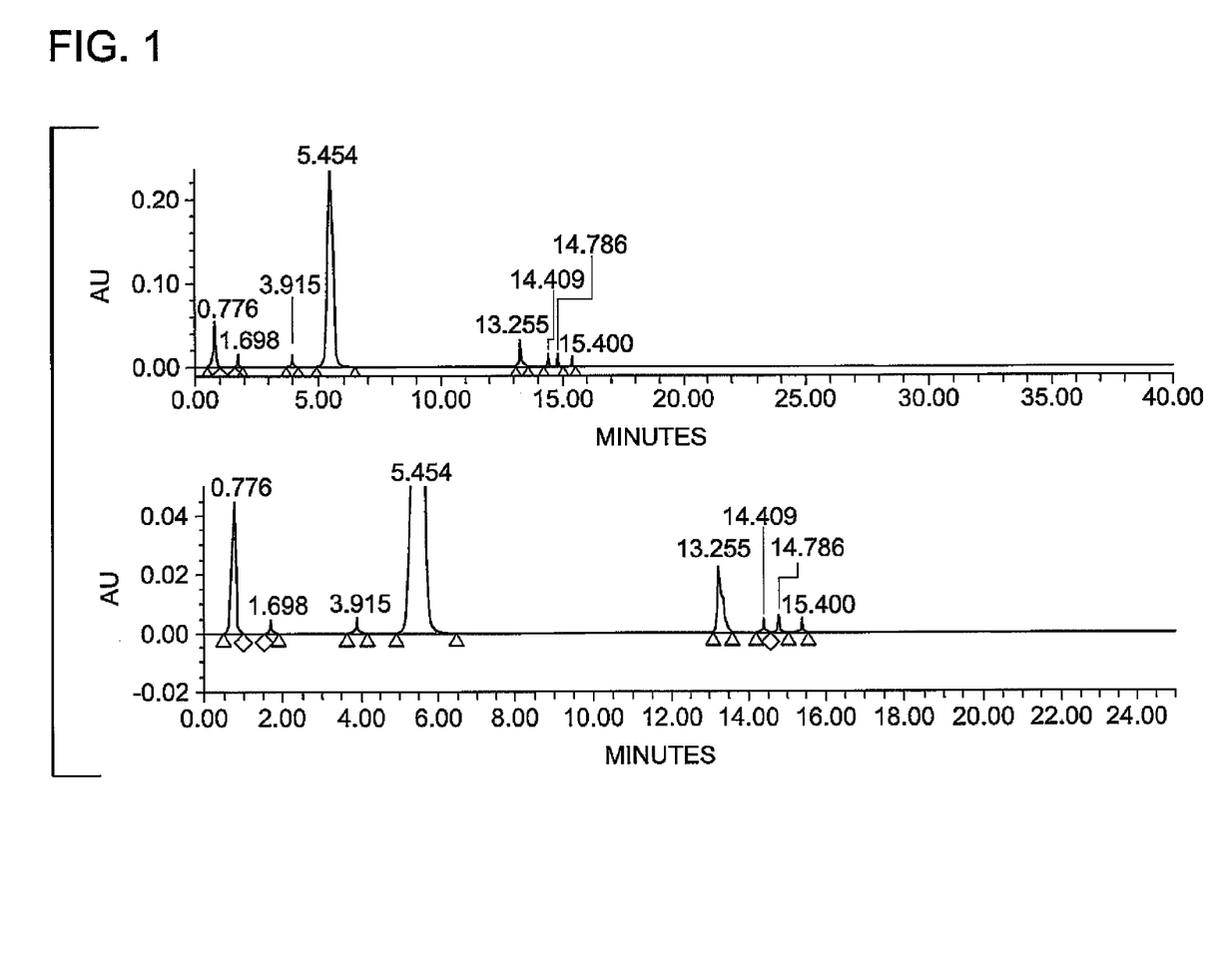
FIG. 1 is an HPLC chromatogram of the reaction mixture produced in Example 3, Experiment 1, depicting peaks at 0.776 minutes (7.55 area %), 1.698 minutes (0.19 area %), 3.915 minutes (0.44 area %), 5.454 minutes (86.75 area %), 13.255 minutes (4.44 area %), 14.409 minutes (0.18 area %), 14.786 minutes (0.34 area %) and 15.400 minutes (0.12 area %).
Figure 2:
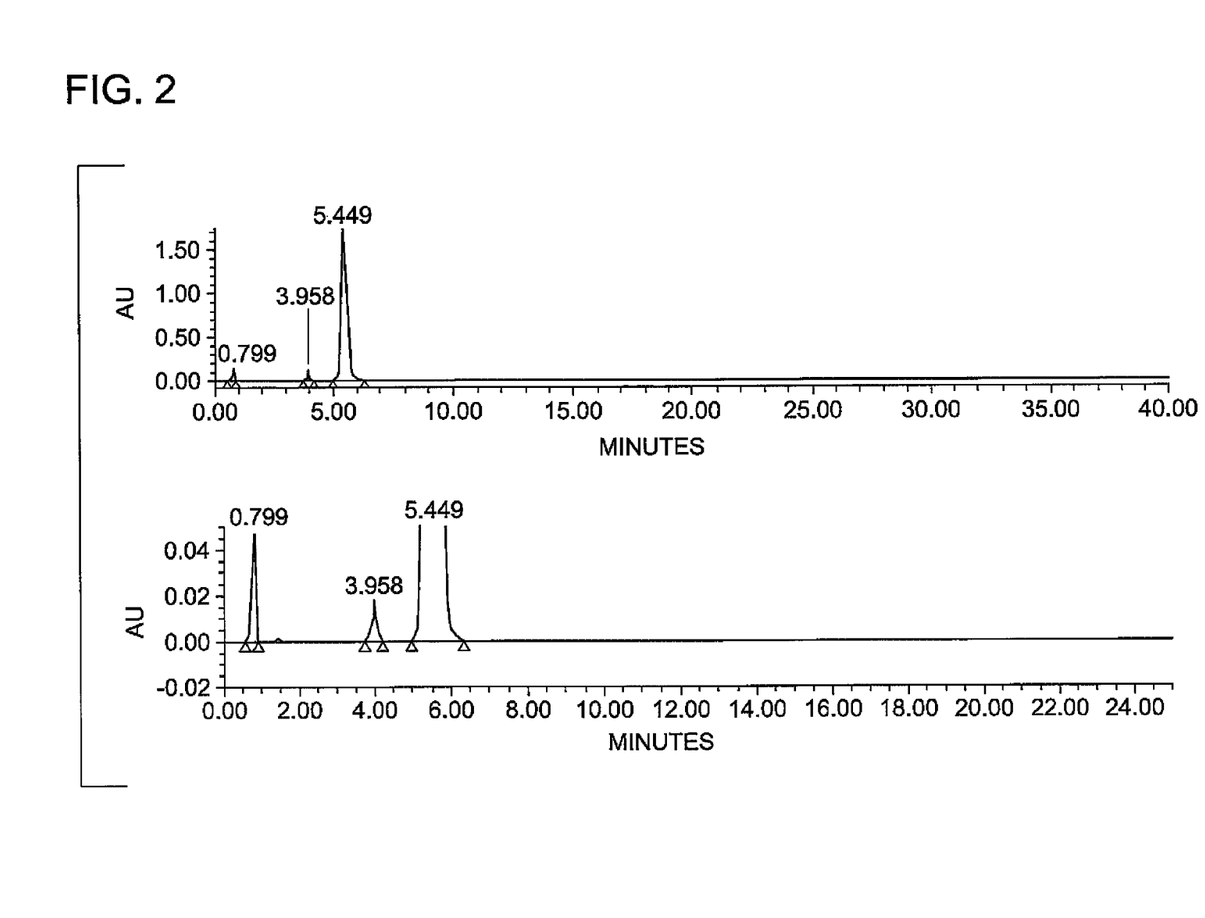
FIG. 2 is an HPLC chromatogram of the reaction mixture produced in Example 3, Experiment 5, depicting peaks at 0.799 minutes (1.23 area %), 3.958 minutes (0.57 area %) and 5.449 minutes (98.20 area %).

The HPLC profiles for experiments 1-3 run at 65° C. and 108° C. showed an increased number of minor peaks as compared to experiments 4-8 run at 25-30° C. and 45-50° C., indicating that the higher reaction temperature, qualitatively, generated a larger number of impurities. In particular, an HPLC chromatogram for experiment 1, depicted in FIG. 1, shows minor peaks at 1.698, 13.255, 14.409, 14.786 and 15.400 minutes whereas an HPLC chromatogram for experiment 5, depicted in FIG. 2, shows an absence of such minor peaks. Further, the diamide prepared at 65° C. and 108° C. had an increase in color as compared to the lower temperature reactions.

When introducing elements of the present invention or the preferred embodiment(s) thereof; the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above methods and compositions (including concentrations of reagents, etc.) without departing from the scope of the present disclosure, it is intended that all matter contained in the above description shall be interpreted as illustrative and not limiting in any sense.

What is claimed is:

1. A process for preparing a diamide compound of formula (2), the process comprising:

(i) forming a reaction mixture comprising a diester of formula (1), (1)

a primary amine of formula RNH$_2$, a basic catalyst and a solvent; and (ii) heating the reaction mixture to a reaction temperature of from about 25° C. to less than 65° C. and holding the reaction mixture at the reaction temperature for a reaction time sufficient to generate a reaction product mixture comprising diamide compound formula (2)

wherein,

R, $R^1$ and $R^2$ independently selected from $C_1$ to $C_{18}$ straight or branched chain hydrocarbyl or substituted hydrocarbyl, and the molar ratio of the primary amine to the diester is from 2:1 to about 2.4:1;

wherein the reaction product mixture comprises the diamide of formula (2) and at least one of the diester of formula (1), an acid amide of formula (3), an amide ester of formula (4) or an amide ester of formula (5)

wherein the wherein the content of the acid amide of formula (3) is about 2% or or less, by weight of the sum of the content of formulae (1) through (5).

2. R is selected from 2-hydroxyethyl, 2,3-dihydroxypropyl, 3-hydroxypropyl, 3,4-dihydroxybutyl, 4-hydroxybutyl and 1,3-dihydroxy isopropyl.

3. The process of claim 1, wherein $R^1$ and $R^2$ are independently selected from methyl, ethyl, n-propyl, i-propyl, n-butyl, i-butyl and t-butyl.

4. The process of claim 1, wherein the solvent comprises methanol, ethanol, 1-propanol, 2-propanol, 1-butanol, 2-butanol, 2-methoxymethanol, 2-ethoxyethanol, 3-methoxypropanol, formamide, N-methylformamide, or combinations thereof.

5. The process of claim 1, wherein the basic catalyst is a salt of an alkali metal and an alkoxide or an alkaline earth metal and an alkoxide.

6. The process of claim 5, wherein the metal is selected from sodium, potassium, lithium and magnesium, and the alkoxide is selected from methoxide, ethoxide, i-propoxide, t-butoxide and amoxide.

7. The process of claim 1, wherein the molar ratio of the primary amine to the diester is from 2:1 to about 2.4:1, from about 2.1:1 to about 2.2:1, from about 2.1:1 to about 2.3:1, or between about 2:1 and about 2.1:1.

8. The process of claim 1, wherein the molar ratio of the catalyst, on an equivalent basis, to the diester is from about 0.03:1 to about 0.1:1, from about 0.04:1 to about 0.1:1, from about 0.05:1 to about 0.09:1, or from about 0.06:1 to about 0.08:1.

9. The process of claim 1, wherein the concentration of the diester of formula (1) in the reaction mixture is from about 1 to about 10 moles per liter, from about 2 to about 10 moles per liter, from about 3 to about 10 moles per liter, from about 4 to about 10 moles per liter, or from about 4 to about 8 moles per liter.

10. The process of claim 1, wherein the reaction temperature is from about 25° C. to about 60° C., from about 25° C. to about 50° C., from about 25° to about 40° C., from about 25° C. to about 35° C., or from about 30° C. to about 40° C.

11. The process of claim 1, wherein the reaction time is from about 1 hour to about 12 hours, from about 1 hour to about 8 hours, from about 1 hour to about 6 hours, from about 1 hour to about 4 hours, from about 1 hour to about 3 hours, from about 1 hour to about 2 hours, from about 2 hours to about 6 hours, or from about 2 hours to about 4 hours.

12. The process of claim 1, wherein the content of the diamide of formula (2) is about 95%, about 96%, about 97%, about 98%, about 99% or more by weight of the sum of the content of formulae (1) through (5), as measured by high pressure liquid chromatography.

13. The process of claim 1, wherein the content of the diester of formula (1) is about 1%, about 0.5%, about 0.3%, about 0.1%, about 0.05%, about 0.03%, about 0.01%, or less by weight of the sum of the content of formulae (1) through (5), or is non-detectable by high pressure liquid chromatography.

14. The process of claim 1, wherein the content of the amide ester of formulae (4) and (5) is about 0.5%, about 0.3%, about 0.1%, about 0.08% about 0.06%, about 0.04%, about 0.02%, about 0.01% or less by weight of the sum of the content of formulae (1) through (5), or is non-detectable by high pressure liquid chromatography.

15. The process of claim 1, wherein:
R is 2,3-dihydroxypropyl;
$R^1$ and $R^2$ are —-$CH_3$;
the catalyst is sodium methoxide;
the solvent comprises methanol;
the molar ratio of the primary amine to the diester is from about 2.04 to about 2.08;
the molar ratio of the catalyst, on an equivalent basis, to the diamide is from about 0.05:1 to about 0.09:1;
the reaction temperature is from about 25° C. to about 40° C.; and
the reaction time is from about 1 hour to about 3 hours.

16. The process of claim 15, wherein the content of the diamide of formula (2) is at least about 96% by weight, the content of the diester of formula (1) is less than about 0.1% by weight, the content of the acid amide of formula (3) is less than about 2% by weight, and the content of the amide ester of formulae (4) and (5) is less than about 0.1% by weight of the content of the sum of the content of formulae (1) through (5).

17. The process of claim 1, further comprising
isolating the diamide compound of formula (2);
purifying the isolated diamide compound; and
reducing the purified diamide compound by hydrogenation
to form a 5-amino isophthalamide of formula (6):

(6)

18. The process of claim 17, wherein the purification is carried out by ion exchange chromatography.

* * * * *